(12) United States Patent
Chang et al.

(10) Patent No.: US 10,029,974 B2
(45) Date of Patent: Jul. 24, 2018

(54) METHOD AND APPARATUS FOR MANUFACTURING CONTINUOUS ACRYLIC ACID THROUGH PROPANE PARTIAL OXIDATION REACTION

(71) Applicant: LG CHEM, LTD., Seoul (KR)

(72) Inventors: Kwang-Hyun Chang, Daejeon (KR); Young-Chang Byun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/510,194

(22) PCT Filed: Oct. 7, 2015

(86) PCT No.: PCT/KR2015/010632
§ 371 (c)(1),
(2) Date: Mar. 9, 2017

(87) PCT Pub. No.: WO2016/056851
PCT Pub. Date: Apr. 14, 2016

(65) Prior Publication Data
US 2017/0297994 A1    Oct. 19, 2017

(30) Foreign Application Priority Data

Oct. 7, 2014 (KR) .................. 10-2014-0134847
Oct. 7, 2015 (KR) .................. 10-2015-0141252

(51) Int. Cl.
| | |
|---|---|
| *C07C 51/215* | (2006.01) |
| *B01J 27/057* | (2006.01) |
| *B01J 8/02* | (2006.01) |
| *B01J 37/00* | (2006.01) |
| *B01J 37/08* | (2006.01) |
| *C07C 51/44* | (2006.01) |

(52) U.S. Cl.
CPC .............. *C07C 51/215* (2013.01); *B01J 8/02* (2013.01); *B01J 27/0576* (2013.01); *B01J 37/0045* (2013.01); *B01J 37/08* (2013.01); *C07C 51/44* (2013.01)

(58) Field of Classification Search
CPC ....... C07C 51/215; C07C 51/44; C07C 51/43; B01J 8/02; B01J 27/0576; B01J 37/0045; B01J 37/08; B01J 23/42; B01J 23/44; B01J 23/46
See application file for complete search history.

(56) References Cited

U.S. PATENT DOCUMENTS

| | | | | |
|---|---|---|---|---|
| 6,114,278 | A * | 9/2000 | Karim | B01J 23/62 502/240 |
| 6,426,433 | B1 * | 7/2002 | Machhammer | C07C 45/33 562/545 |
| 6,492,548 | B1 | 12/2002 | Brockwell et al. | |
| 7,198,766 | B1 * | 4/2007 | Okazaki | B01J 19/0013 422/198 |
| 2009/0287019 | A1 * | 11/2009 | Hazin | B01J 23/002 562/598 |
| 2010/0174112 | A1 | 7/2010 | Nakajima et al. | |
| 2013/0131380 | A1 * | 5/2013 | Dubois | B01J 23/8906 562/545 |

FOREIGN PATENT DOCUMENTS

| | | |
|---|---|---|
| EP | 0495504 A2 | 7/1992 |
| KR | 10-1992-0010470 B1 | 11/1992 |
| KR | 10-2000-0005139 A | 1/2000 |
| KR | 10-2012-0025471 A | 3/2012 |
| KR | 10-2013-0080434 A | 7/2013 |

* cited by examiner

*Primary Examiner* — Pancham Bakshi
*Assistant Examiner* — Mark R Luderer
(74) *Attorney, Agent, or Firm* — Dentons US LLP

(57) ABSTRACT

This invention relates to a method of continuously preparing acrylic acid and an apparatus using the same, the method including: (1) subjecting a feed including propane, oxygen, water vapor and carbon dioxide to partial oxidation using a catalyst, thus obtaining an acrylic acid-containing mixed gas, (2) separating the acrylic acid-containing mixed gas into an acrylic acid-containing solution and a gas byproduct, (3) separating an acrylic acid solution from the separated acrylic acid-containing solution, and (4) recycling the separated gas byproduct into the feed.

18 Claims, 2 Drawing Sheets

US 10,029,974 B2

METHOD AND APPARATUS FOR MANUFACTURING CONTINUOUS ACRYLIC ACID THROUGH PROPANE PARTIAL OXIDATION REACTION

TECHNICAL FIELD

This application is the National Stage entry of International Application No. PCT/KR2015/010632 filed Oct. 7, 2015, which claims the benefit of Korean Patent Application Nos. 10-2014-0134847, filed Oct. 7, 2014, and 10-2015-0141252, filed Oct. 7, 2015, which are hereby incorporated by reference in their entirety into this application.

The present invention relates to a method and apparatus for continuously preparing acrylic acid through partial oxidation of propane.

BACKGROUND ART

Acrylic acid is useful as a binder, and acrylic acid is an important chemical used for the use such as a monomer for preparing a polymer that is used by being dispersed in an aqueous medium.

Acrylic acid is mainly prepared in a manner in which propylene is primarily oxidized to acrolein, which is then subsequently oxidized.

Specifically, FIG. 1 shows the process of producing acrylic acid (AA) from propylene. As shown in this drawing, propylene is reacted with oxygen in air using a Mo—Bi-based first-step catalyst and a Mo—W-based second-step catalyst and is thus almost completely consumed (conversion of 97% or more). Among reaction products, a condensable oxygenated product including AA is condensed into a liquid phase in an absorption tower and then transferred to an AA separation tower. About 30% of a stream, including not only unreacted propylene but also nitrogen ($N_2$), oxygen ($O_2$), carbon monoxide (CO), carbon dioxide ($CO_2$) and water ($H_2O$), is recycled. The recycled stream contains a large amount of nitrogen ($N_2$), about 25 to 30 vol % of water ($H_2O$), and small amounts of oxygen ($O_2$), carbon monoxide (CO) and carbon dioxide ($CO_2$). The recycled stream is mixed with propylene and air at the inlet of a reactor and is then introduced to the reactor, and about 70% of the remainder thereof is purged and then incinerated in an incinerator. The stream supplied into the reactor, together with the recycled stream, has the following composition at the reactor inlet: 7% propylene, 12.6% oxygen ($O_2$) (from air), 72.4% nitrogen ($N_2$) (47.4% from air and 25% from the recycled stream), and 8% water ($H_2O$) (from the recycled stream).

A propane-based acrylic acid production process (POA) for preparing acrylic acid from propane has not yet been commercialized because of low propane conversion and acrylic acid selectivity. FIG. 2 schematically shows a propane-based acrylic acid production process, to which a propylene-based acrylic acid production process is applied without change. This method suffers from excessive loss of unreacted propane. For example, U.S. Pat. No. 7,304,014 discloses a propane conversion of 68% and an acrylic acid selectivity of 80% through a single pass, but is problematic in that when the propane-based acrylic acid production process is applied to the propylene-based acrylic acid production process, only 30% of the 32% unreacted propane fraction is recycled, and the remaining 70% thereof is purged in an incinerator, undesirably resulting in propane loss of 22.4% (0.32*70).

A catalyst mainly used in the propane-based process is MoVTeNb. In the presence of a MoVTeNb-based catalyst, when the propane/$O_2$ ratio is high, propane conversion is lowered. On the other hand, when the propane/$O_2$ ratio is low, the propane conversion is increased, but $CO_x$ selectivity, such as CO, $CO_2$, etc. is increased, that is, the selectivity of oxygenated carbon, is increased, thus decreasing an acrylic acid yield or an acrylic acid selectivity.

A currently available propane-based acrylic acid production process is problematic because of the large amounts of unreacted propane and non-condensable gas, such as CO, $CO_2$ or propylene, undesirably causing excessive energy expense upon separation of byproducts and requiring an additional unit for removing CO and $CO_2$.

DISCLOSURE

Technical Problem

In a currently available propane-based acrylic acid production process, nitrogen is used as a carrier gas. However, when the nitrogen carrier gas is used, $CO_x$ has to be additionally separated from byproducts in order to recycle unreacted propane, and also, oxygen ($O_2$) has to be added instead of air. In the case where $CO_x$ is not separated, the loss of unreacted propane is high, as shown in FIG. 2.

Also, in order to increase the conversion, when the propane/$O_2$ ratio is decreased, a lot of energy is required to separate CO and $CO_2$, which are generated in large amounts. Furthermore, the acrylic acid yield is remarkably low.

Therefore, the present invention is intended to provide a method of preparing acrylic acid through the partial oxidation of propane, which consumes less energy and is less expensive. In addition, the present invention is intended to provide a method of preparing acrylic acid, which may prevent coke deposition on a catalyst used for partial oxidation of propane.

Also, the present invention is intended to provide a method of continuously preparing acrylic acid, which may prevent the internal temperature of a reactor from excessively increasing and additional byproducts from being generated.

Also, the present invention is intended to provide a method of continuously preparing acrylic acid, in which byproducts may be used through recycling.

Technical Solution

An aspect of the present invention provides a method of continuously preparing acrylic acid, comprising the steps of: (1) subjecting a feed including propane, oxygen, water vapor and carbon dioxide to partial oxidation using a catalyst, without the use of nitrogen, thus obtaining an acrylic acid-containing mixed gas; (2) separating the acrylic acid-containing mixed gas into an acrylic acid-containing solution and a gas byproduct using an absorption solvent; (3) separating the separated acrylic acid-containing solution into an acrylic acid solution and a liquid byproduct through purification; and (4) recycling the separated gas byproduct into the feed without additional separation.

In a preferred embodiment of the present invention, the gas byproduct may include at least one selected from the group consisting of propane, propylene, oxygen, carbon monoxide, carbon dioxide, and water vapor, and the recycling gas byproduct may be recycled so as to be suitable for the molar ratio of the feed. The composition molar ratio of the feed including the separated gas byproduct of step (4)

may be maintained so as to be suitable for the composition molar ratio of the feed in step (1).

In a preferred embodiment of the present invention, oxidizing carbon monoxide into carbon dioxide using a catalyst including at least one selected from the group consisting of rhodium (Rh), iridium (Ir), palladium (Pd), and platinum (Pt) may be further performed between steps (1) and (2).

Another aspect of the present invention provides an apparatus for continuously preparing acrylic acid, comprising: (1) a partial oxidation reactor configured to prepare an acrylic acid-containing mixed gas by subjecting a feed including propane, oxygen, water vapor and carbon dioxide, transferred via a feed transfer line, to partial oxidation using a catalyst; (2) an absorption tower configured to separate the acrylic acid-containing mixed gas into an acrylic acid-containing solution and a gas byproduct and to absorb the acrylic acid-containing solution; (3) a distillation tower configured to separate the acrylic acid-containing solution into an acrylic acid solution; and (4) a recycling transfer line configured to recycle the separated gas byproduct.

Advantageous Effects

According to the present invention, a method of preparing acrylic acid through partial oxidation of propane, which consumes less energy and is less expensive, can be provided. Furthermore, this method is capable of preventing coke deposition on a catalyst, an excessive increase of the internal temperature of a reactor, and additional conversion into $CO_x$ and oxygenated compounds.

Further, according to the present invention, byproducts other than acrylic acid can be used through recycling. Specifically, in the present invention, when carbon dioxide ($CO_2$) is used as a carrier gas, unreacted propane can be almost completely recycled without an additional separation unit to remove carbon dioxide ($CO_2$). Thus, the method of continuously preparing acrylic acid is favorable because of a simple preparation process and remarkably decreased production cost.

BEST MODE

Figure 1:
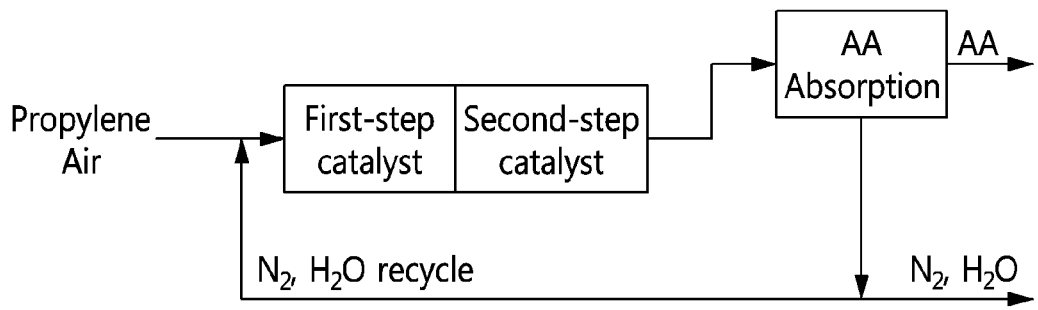
FIG. 1 shows a propylene-based acrylic acid production process.
Figure 2:
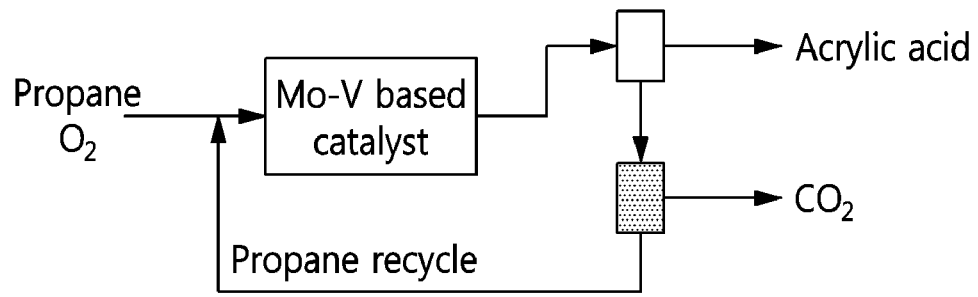
FIG. 2 schematically shows an exemplary propane-based acrylic acid production process (POA), to which a propylene-based AA production process is applied without change.

Hereinafter, a detailed description will be given of the present invention. The following description is merely set forth to illustrate embodiments of the present invention, but is not to be construed as limiting the scope defined by the claims, even if it contains restrictive expressions.

In a method of preparing acrylic acid using a propane-based process, when nitrogen is used as a carrier gas, the additional separation not only of $CO_x$ but also of nitrogen from byproducts is required, which is undesirable. Also, economic benefits may be negated due to the high loss of unreacted propane.

Accordingly, the present inventors have discovered the fact that the above problems are solved by using carbon dioxide ($CO_2$) as a carrier gas during the partial oxidation of propane, thus culminating in the present invention.

Thus, an aspect of the present invention addresses a method of continuously preparing acrylic acid, comprising the steps of (1) subjecting a feed including propane, oxygen, water vapor and carbon dioxide to partial oxidation using a catalyst, thus obtaining an acrylic acid-containing mixed gas; (2) separating the acrylic acid-containing mixed gas into an acrylic acid-containing solution and a gas byproduct; (3) separating an acrylic acid solution from the acrylic acid-containing solution; and (4) recycling the separated gas byproduct into the feed.

In the present invention, the term "acrylic acid-containing mixed gas" refers to a mixed gas, which may be generated upon the preparation of acrylic acid through partial oxidation.

For example, a POA process operating in the presence of a catalyst that exhibits a propane conversion of 60%, an AA selectivity of 80%, and a $CO_2$ selectivity of 20% is exemplified as follows. The condensable oxygenated product including AA is condensed into a liquid in an absorption tower and is then transferred to an AA separation tower, and most (96%) of carbon dioxide ($CO_2$) stream including unreacted propane is recycled, only a small amount (4%) thereof being purged. That is, some thereof is purged and removed in an amount corresponding to the amount of carbon dioxide ($CO_2$) that is produced through POA catalysis. The fact that CO2 is main byproduct which is not condensed in acrylic acid adsorption unit is utilized. Specifically, the amount of water ($H_2O$) in the recycled stream may be about 25 to 30 vol %. Thus, the feed at the inlet of the reactor may be composed of about 7% propane, 14% $O_2$ (as molecular $O_2$), 50 to 59% $CO_2$, and 20 to 29% $H_2O$.

If the amount of water is greater than 25 to 30 vol %, the carbon dioxide ($CO_2$) stream discharged from the absorption tower may contain a large amount of volatile byproduct. On the other hand, if the amount thereof is less than 25 vol %, an excessive amount of water must be used upon absorption, and thus a lot of energy is required in the separation process.

Below is a description of the method of preparing acrylic acid according to the present invention.

According to an embodiment of the present invention, the method of preparing acrylic acid includes (1) obtaining an acrylic acid-containing mixed gas through partial oxidation.

The acrylic acid-containing mixed gas may be obtained by subjecting the feed including propane, oxygen, water vapor and carbon dioxide to partial oxidation in the presence of a catalyst, as defined above. The partial oxidation may be a gaseous reaction, and the gaseous oxidation reaction may be carried out under typical conditions using a typical partial oxidation reactor in the technical field to which the present invention belongs (which is hereinafter referred to as "the art").

In the present invention, propane is a raw material for producing acrylic acid, and oxygen functions as an oxidant for partially oxidizing propane.

In the present invention, the term "partial oxidation" means that a material is not completely oxidized but is partially oxidized, thus producing not only a desired oxidized material but also an unreacted material and byproducts.

In a preferred embodiment of the present invention, the molar ratio of propane to oxygen may range from 1:0.5 to 3, and preferably from 1:1 to 2.5. If the molar ratio of oxygen is less than 0.5, the amount of oxygen for conversion into desired acrylic acid is too small, and thus low conversion and selectivity may result, and a large-capacity unit for recycling unreacted propane is required. On the other hand, if the molar ratio of oxygen exceeds 3, the propane conversion may increase but the selectivities of carbon dioxide ($CO_2$), carbon monoxide (CO), acetic acid, and propionic acid may increase, undesirably deteriorating the acrylic acid yield. Hence, the molar ratio thereof is preferably set to the above range.

Meanwhile, in the present invention, propane may be oxidized into acrylic acid, as shown in Scheme 1 below.

  [Scheme 1]

In a preferred embodiment of the present invention, the partial oxidation may be carried out at 200 to 500° C., and preferably at 300 to 450° C.

If the reaction temperature is lower than 200° C., the energy for activating propane is low, and thus the reaction may not occur. On the other hand, if the reaction temperature is higher than 500° C., acrylic acid produced through partial oxidation may be further oxidized into carbon monoxide (CO) and carbon dioxide ($CO_2$), thus decreasing selectivity. Hence, the reaction temperature is preferably set to the above range.

In the partial oxidation according to the present invention, the reaction pressure is 0 to 75 psig, and preferably 5 to 50 psig. Given the above pressure range, low processing cost and high reaction selectivity may result.

Next, water vapor is described.

The water vapor functions to increase acrylic acid selectivity and to change the explosion limit of propane to thus improve catalyst stability.

The water vapor may be contained in an amount of 5 to 50 mol %, preferably 10 to 40 mol %, and more preferably 15 to 30 mol %, based on the total mol % of the feed.

If the amount of water vapor is less than 5 mol %, coke formed due to propane may be deposited on the catalyst, thus deactivating the catalyst. The term "coke" indicates a carbon deposit resulting from reducing a hydrocarbon, as commonly used by those skilled in the art. On the other hand, if the amount of water vapor exceeds 50 mol %, the amount of coke deposited on the catalyst may be decreased but the amount of propane added into the reactor may be lowered, undesirably resulting in low acrylic acid productivity. Furthermore, in order to maintain the amount of water vapor constant during the reaction, separating the discharge gas should be additionally performed after the reaction. Hence, the molar amount of water vapor is preferably set to the above range.

Next, carbon dioxide is described.

In the present invention, carbon dioxide is a carrier gas, and acts as a mild oxidant having lower oxidizing power than that of oxygen so as to oxidize the coke deposited on the catalyst.

In the present invention, the mild oxidant, namely carbon dioxide, has oxidizing power lower than that of oxygen ($O_2$) or carbon monoxide (CO), and has high ability to oxidize other materials and to reduce itself.

Also, carbon dioxide has higher heat capacity than that of nitrogen ($N_2$) and water ($H_2O$) and thus plays a role in mitigating an increase in the internal temperature of the reactor during partial oxidation.

Generally, nitrogen ($N_2$) is used as a carrier gas in the preparation of acrylic acid. In order to recycle nitrogen ($N_2$), separating nitrogen from byproducts and supplying air to compensate for the lack of nitrogen have to be further performed. Thus, the preparation apparatus further requires a separation unit and a compressor for supplying pure nitrogen or air as a nitrogen source to compensate for the lack of nitrogen. When the carrier gas is nitrogen ($N_2$), the catalyst used for the partial oxidation of propane is acidic, and thus coke may be deposited, undesirably deactivating the catalyst.

However, in the present invention, carbon dioxide is used as a carrier gas, thus obviating the above additional steps and/or units. Accordingly, processing costs are decreased without the need for additional steps and/or units, thus lowering preparation costs. When carbon dioxide having oxidizing power is used as a carrier gas, coke on the catalyst is oxidized into $CO_x$, making it possible to prevent coke deposition on the catalyst. Furthermore, carbon dioxide contained in the byproducts of the partial oxidation is used again, thereby obviating the step and/or unit for continuously supplying the carbon dioxide feed during the continuous preparation of acrylic acid. Hence, low processing costs and simple processing may result, thus increasing processing efficiency.

Since partial oxidation of propane by oxygen ($O_2$) is exothermic, the heat that is generated has to be removed in order to prevent the temperature from excessively increasing. Here, the carrier gas and/or water vapor may function to absorb such heat, and nitrogen ($N_2$) has a heat capacity of 22.1 kJ/kmol.K at 400° C. and water vapor has a heat capacity of 37.1 kJ/kmol.K at 400° C. In contrast, the heat capacity of carbon dioxide ($CO_2$) is 48.9 kJ/kmol.K at 400° C., and is higher than those of nitrogen ($N_2$) and water vapor at the partial reaction temperature of about 200 to 500° C. Hence, an excessive temperature increase is prevented and additional conversion into $CO_x$ and oxygenated compounds may be prevented.

In a preferred embodiment of the present invention, carbon dioxide may be contained in an amount of 40 to 80 mol %, preferably 45 to 75 mol %, and more preferably 40 to 70 mol % based on the total mol % of the feed. If the amount of carbon dioxide is less than 40 mol %, the range that may inhibit an increase in the internal temperature of the reactor is low, and thus additional coolant is required to decrease the internal temperature of the reactor. On the other hand, if the amount of carbon dioxide exceeds 80 mol %, the amount of propane for the preparation of acrylic acid is decreased, undesirably lowering acrylic acid productivity per volume of the reactor. Hence, the molar amount of carbon dioxide is preferably set to the above range.

The catalyst is described below.

The catalyst for the partial oxidation of the present invention may include those typically useful in the art, and preferably used is a catalyst represented by Chemical Formula 1 below. However, the present invention is not limited thereto.

In the present invention, the catalyst represented by Chemical Formula 1 below may be used. The reason why the following catalyst is used is that the highest acrylic acid yield may be exhibited despite evaporation of tellurium (Te) at high temperatures.

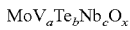  [Chemical Formula 1]

In Chemical Formula 1, a, b, c and x are proportions relative to 1 of Mo.

In Chemical Formula 1, a is a number from 0.006 to 1, and preferably from 0.09 to 0.8. b is a number from 0.006 to 1, and preferably 0.04 to 0.6, and c is a number from 0.006 to 1, and preferably 0.01 to 0.4. Also, x is the amount of oxygen bound to the other elements, and depends on their oxidation state.

In Chemical Formula 1, Mo is molybdenum, V is vanadium, Te is tellurium, Nb is niobium, and O is oxygen.

The catalyst of Chemical Formula 1 undergoes low reduction during the partial oxidation of the present invention, and is oxidized again through reaction with gaseous oxygen. The activity thereof is slightly decreased, but may be easily regenerated through heating in the presence of oxygen, water vapor and carbon dioxide after use for a predetermined period of time. After the regeneration, the initial activity of the catalyst can be restored, and the catalyst may be used for other reaction cycles.

In an embodiment of the present invention, the catalyst may be placed in a multi-tube reactor in order to prevent the reaction temperature from drastically increasing.

The catalyst of Chemical Formula 1 according to the present invention is prepared as follows.

50 ml of distilled water at 35° C. is added with 0.234 g of ammonium metavanadate, 0.352 g of telluric acid, and 1.178g of ammonium paramolybdate to give a clear solution. The solution is added with 0.348 g of ammonium niobium oxalate pre-dissolved in 8 ml of distilled water and then mixed. The resulting mixture is mixed with stirring for 3 hr, and then added with sulfuric acid. The solvent in the slurry thus prepared is evaporated using a rotary evaporator, and the slurry is completely dried in an oven at 120° C., ground to make pellets, sieved to 180 to 250 µm, and fired at 200° C. for 2 hr in an air atmosphere and at 600° C. for 2 hr in a nitrogen atmosphere. This method is exemplary for the preparation of the catalyst from the slurry, or alternatively, the catalyst may be prepared through hydrothermal processing in an autoclave, filtration, drying, and firing.

Next, step (2) is described.

The acrylic acid-containing mixed gas produced through the partial oxidation in step (1) may include not only a target product, namely acrylic acid, but also organic and/or inorganic byproducts. Examples of the organic byproducts may include acrolein, propionic acid, acetone, acetic acid, high-boiling-point byproducts, unreacted propane and/or propylene, and examples of the inorganic byproducts may include carbon monoxide, carbon dioxide and water vapor.

In step (2) of the present invention, the acrylic acid-containing mixed gas produced in step (1) is added with an absorption solvent, whereby it may be separated into an acrylic acid-containing solution and a gas byproduct. The separation process using the absorption solvent may be performed without limitation, so long as it is typically useful. The absorption solvent may be used without limitation, so long as it is typically useful, and is preferably water.

In step (2) of the present invention, the gas byproduct has a boiling point lower than that of the absorption solvent and also has low solubility in the absorption solvent used, and thus remains in a gas phase and may be separated. The byproduct contained in the acrylic acid-containing solution has a boiling point that is higher than that of the absorption solvent in step (2) and is lower than the partial oxidation reaction temperature. The byproduct contained in the acrylic acid-containing solution is present in a gas phase at a temperature for partial oxidation, and is then converted from the condensable gas into a liquid phase while coming into contact with the absorption solvent, and is thereby separated.

In a preferred embodiment of the present invention, the separated gas byproduct may include unreacted propane, byproduced propylene, carbon monoxide, carbon dioxide, and water vapor. The acrylic acid-containing solution indicates a solution including the acrylic acid-containing mixed gas excluding the gas byproduct in a liquid phase. The acrylic acid-containing solution may include acrylic acid, acrolein, propionic acid, acetone, acetic acid, and/or a high-boiling-point byproduct.

The gas byproduct may include a trace or small amount of acrylic acid-containing solution in a gas phase, whereas the acrylic acid-containing solution may include a trace or small amount of gas byproduct. This state may vary depending on the absorption conditions, but complete separation of gas byproduct and AA containing solution is preferable.

The acrylic acid-containing solution discharged in step (2) includes 40 to 90 wt %, preferably 50 to 90 wt %, and more preferably 50 to 80 wt % of acrylic acid in order to improve efficiency.

In step (2) of the present invention, the acrylic acid-containing mixed gas is added with water. Then, it is separated into the gas byproduct, including a byproduct having a boiling point lower than the boiling point of water and low solubility in water, and also into the acrylic acid-containing solution including a byproduct having a boiling point higher than the boiling point of water.

Step (2) of the present invention may be performed as described above, but the present invention is not limited thereto.

In a preferred embodiment of the present invention, the gas byproduct may include at least one selected from the group consisting of unreacted propane, byproduced propylene, carbon monoxide, carbon dioxide, and water vapor. Since the gas byproduct has a composition similar to that of the feed, it is neither completely removed nor additionally separated, and may be appropriately used through recycling.

In the gas byproduct, an alkene such as propylene is present in a very small amount, and may be converted into acrylic acid in the presence of the catalyst and does not significantly affect the reaction, and is thus not separated from the other byproducts. Thus, the separation of an alkene from an alkane such as propane is neither essential nor preferable during the processing of the present invention.

The acrylic acid-containing mixed gas and/or the gas byproduct may include carbon monoxide. The carbon monoxide may be generated in an amount approximately identical to that of carbon dioxide. Alternatively, carbon monoxide may be generated in an amount greater than that of carbon dioxide, among the byproducts generated through the partial oxidation of propane using a $MoV_aTe_bNb_cO_x$-based catalyst in the present invention.

Thus, in the case where the method of preparing acrylic acid according to the present invention is continuously performed, the amount of generated carbon monoxide (CO) is greater than the amount of generated carbon dioxide ($CO_2$), and thus carbon monoxide (CO) is accumulated in the reactor with an increase in the reaction time, making it impossible to conduct normal operation. Dangerously, unless carbon monoxide (CO) is converted into carbon dioxide ($CO_2$) through reaction with oxygen in the presence of a POA catalyst, the concentration of carbon monoxide (CO) in a steady state is increased about 24 times compared to that of produced carbon monoxide (CO), and thus the composition of the feed may fall within the explosive range.

Hence, carbon monoxide is preferably oxidized into carbon dioxide.

Before step (2) and after step (1), or during the recycling from step (4) to step (1), oxidizing carbon monoxide into carbon dioxide is preferably further performed. This is because unreacted oxygen, which is not consumed during the partial oxidation of the feed, is reacted with a metal catalyst to thus convert carbon monoxide into carbon dioxide.

In a preferred embodiment of the present invention, oxidizing carbon monoxide into carbon dioxide using a catalyst including at least one selected from the group consisting of rhodium (Rh), iridium (Ir), palladium (Pd) and platinum (Pt) may be further performed between steps (1) and (2).

Also, oxidizing carbon monoxide into carbon dioxide using a catalyst including at least one selected from the group consisting of rhodium (Rh), iridium (Ir), palladium (Pd) and platinum (Pt) may be further performed during the recycling from step (4) to step (1).

Next, step (3) is described.

The organic byproduct contained in the acrylic acid-containing solution separated in step (2) may be separated in order to prevent accumulation thereof during the processing. Thus, in step (3) of the present invention, the acrylic acid-containing solution is purified and thus separated into an acrylic acid solution and a liquid byproduct. The purification in step (3) of the present invention may be performed without limitation, so long as it is typically useful. Preferably used is a distillation process using differences between boiling points, but the present invention is not limited thereto.

In step (3), the acrylic acid-containing solution separated in step (2) is cooled to primarily remove a high-boiling-point byproduct, and then separated into the acrylic acid solution and the liquid byproduct through distillation using heat and an azeotropic solvent. The liquid byproduct may include acrolein, propionic acid, acetone, acetic acid and/or a high-boiling-point byproduct, and the acrylic acid solution may be a solution including only acrylic acid by removing the liquid byproduct. The acrylic acid solution may contain a trace or small amount of liquid byproduct, but preferably contains only acrylic acid.

The separated acrylic acid solution may be subjected to extractive distillation and/or crystallization, thus obtaining acrylic acid, and the liquid byproduct may be removed.

In a preferred embodiment of the present invention, the separated acrylic acid solution is recovered to thus obtain acrylic acid, and the liquid byproduct is separated and removed, and the gas byproduct may be used through recycling.

Next, step (4) is described.

The gas byproduct separated in step (2) may include at least one selected from the group consisting of propane, propylene, oxygen, carbon monoxide, carbon dioxide, and water vapor, and the separated gas byproduct may be recycled. The separated gas byproduct has a composition similar to that of the feed, and may be appropriately used through recycling. Without any further purification or separation, the gas byproduct may be directly recycled into the feed of step (1). Upon recycling into the feed, the gas byproduct may be recycled in the state of being contained in the feed, or may be recycled through another stream, whereby it may be subjected to partial oxidation with the feed.

In a preferred embodiment of the present invention, the feed including the gas byproduct recycled from step (4) may be recycled so as to be suitable for the composition molar ratio of the feed of step (1).

As mentioned above, the molar ratios of the feed are as follows: the molar ratio of propane to oxygen is 1:0.5 to 3, the amount of water vapor is 5 to 50 mol % and the amount of carbon dioxide is 40 to 80 mol %, based on the total mol % of the feed. The composition molar ratio of the feed including the feed of step (1) and the recycling gas byproduct of step (4) is maintained constant so that acrylic acid may be continuously prepared.

The feed including the recycling gas byproduct of step (4) is described in detail below.

The gas byproduct separated in step (2) is recycled in step (4), and the recycling gas byproduct is supplied in the state of being contained in the feed flowing to step (1).

The recycling gas byproduct of step (4) is a byproduct produced or left behind through partial oxidation of the fresh feed in step (1). Specifically, in the present invention, the recycling gas byproduct may include propane, oxygen, water vapor, and carbon dioxide, remaining after partial consumption through partial oxidation of the fresh feed of step (1), and may include water vapor and carbon dioxide, additionally produced through partial oxidation.

Therefore, the recycling gas byproduct may be supplied to the feed of step (1) by removing some of the water vapor and carbon dioxide and by adding only propane and oxygen so as to be suitable for the molar ratio of the feed. The feed necessary for step (1) may be supplied by including only propane and oxygen, which are insufficient in the recycling gas byproduct, as needed. The amount of the supplied feed may be decreased in the feed including the recycling gas byproduct, rather than in the fresh feed.

Consequently, the present invention obviates the additional units and steps for separating carbon dioxide used in the related art. Also, the amount of the feed supplied to continuously prepare acrylic acid may be decreased. Hence, the present invention enables the stable continuous preparation of acrylic acid through temperature control, purging of gas in a trace amount, and supply of the feed in a small amount. Thereby, the present invention is effective at reducing costs and simplifying processing.

Also, the molar ratio of the feed may be adjusted so as to be suitable for desired acrylic acid selectivity and propane conversion.

Meanwhile, the conventional propane-based acrylic acid preparation method exhibits a propane conversion of less than 50% and a very low acrylic acid yield.

However, the method of preparing acrylic acid according to the present invention may exhibit a propane conversion of 40% or more and an acrylic acid selectivity of 70% or more under the same conditions as in the conventional method, with the exception of the carrier gas. The propane conversion and the selectivity are calculated using Equations 1 and 2 below.

Propane conversion (%)=(mol of reacted propane/ mol of supplied propane)×100     [Equation 1]

Acrylic acid selectivity (%)=(mol of produced acrylic acid/mol of reacted propane)×100     [Equation 2]

Although only the conversion is intended to increase in the related art, in the present invention, high selectivity may be maintained even at a similar propane conversion under the same conditions as in the related art. Furthermore, the feed may be recycled to thus ensure a high acrylic acid yield. Moreover, some of the byproduct may be recycled, thus reducing costs.

Another aspect of the present invention addresses an apparatus for continuously preparing acrylic acid, comprising (1) a partial oxidation reactor configured to prepare an acrylic acid-containing mixed gas by subjecting a feed including propane, oxygen, water vapor and carbon dioxide, transferred through a feed transfer line, to partial oxidation using a catalyst; (2) an absorption tower configured to separate the prepared acrylic acid-containing mixed gas into an acrylic acid-containing solution and a gas byproduct and to absorb the acrylic acid-containing solution; (3) a distillation tower configured to separate the acrylic acid-containing solution into an acrylic acid solution; and (4) a recycling transfer line configured to recycle the separated gas byproduct.

The recycling transfer line may be connected to the feed transfer line. Alternatively, the recycling transfer line may be connected to the partial oxidation reactor.

In a preferred embodiment of the present invention, an oxidation unit containing a catalyst including at least one selected from the group consisting of rhodium (Rh), iridium (Ir), palladium (Pd) and platinum (Pt) may be further provided.

In another preferred embodiment of the present invention, a control unit configured to control the recycling gas byproduct so as to be suitable for the composition molar ratio of the feed may be further provided. The control unit may be provided to the recycling transfer line.

The apparatus for continuously preparing acrylic acid may use the method of continuously preparing acrylic acid according to the present invention. Thus, a description of the amounts of propane, oxygen, water vapor and carbon dioxide, the gas byproduct, the catalyst, the partial oxidation temperature, and the absorption solvent may remain the same as above.

The method of preparing acrylic acid through partial oxidation of propane according to the present invention may be performed using a static apparatus, a dynamic apparatus or a combination thereof, typically useful in the art. For example, it may be conducted in a preparation apparatus including a partial oxidation reactor, an oxidation unit, an absorption tower, a control unit, a distillation tower, and transfer lines, and further including an organic byproduct absorption tower and/or a cooling tower. However, the present invention is not limited thereto.

Figure 3:
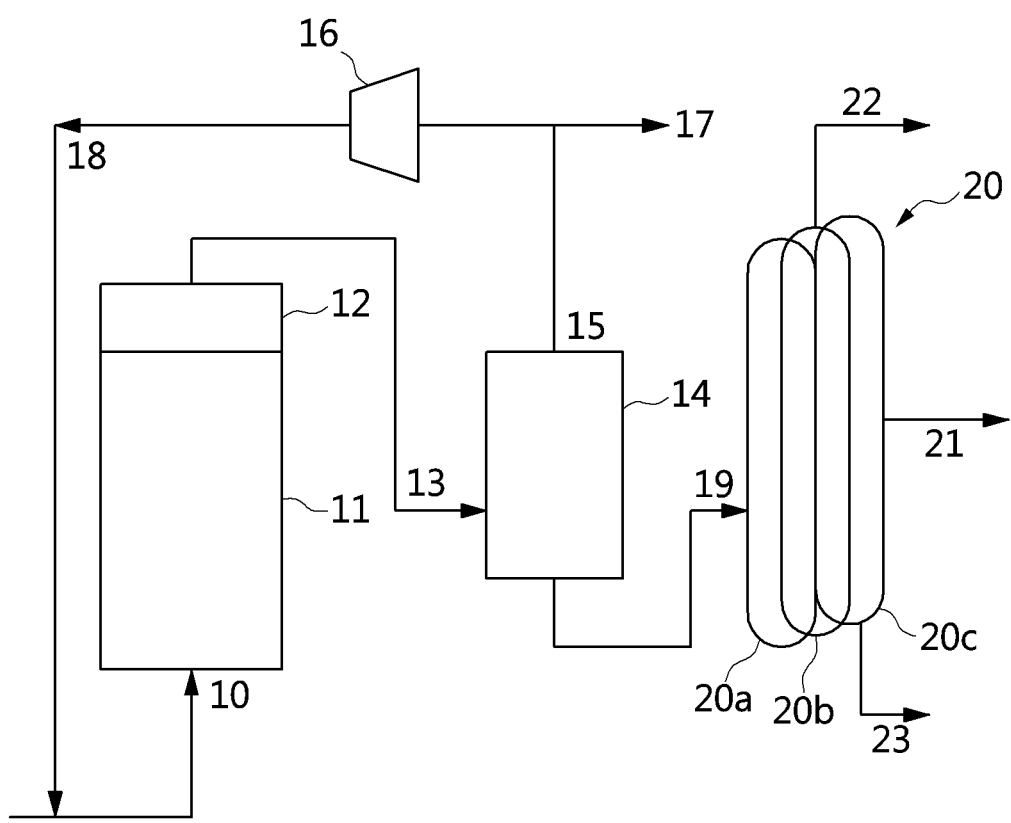
FIG. 3 schematically shows an apparatus for performing a process of preparing acrylic acid according to a preferred embodiment of the present invention.

FIG. 3 shows an apparatus for preparing acrylic acid, including a partial oxidation reactor of propane, while recycling a gas byproduct according to an embodiment of the present invention. The apparatus includes a partial oxidation reactor 11, an oxidation unit 12, an absorption tower 14, a control unit 16 and a distillation tower 20, and also transfer lines 10, 13, 15, 17, 18, 19, 21, 22, 23 for connecting respective units.

Specifically, the feed including propane, oxygen, water vapor and carbon dioxide is subjected to partial oxidation in the partial oxidation reactor 11 including a catalyst by means of the feed transfer line 10, thus preparing an acrylic acid-containing mixed gas. While the prepared acrylic acid-containing mixed gas is passed through the oxidation unit 12 including a Pt catalyst layer, carbon monoxide is oxidized into carbon dioxide. Then, the acrylic acid-containing mixed gas is passed through the absorption tower 14 for spraying water from the top thereof, and is thus separated into an acrylic acid-containing solution and a gas byproduct. The acrylic acid-containing solution is transferred into the distillation tower 20 via the transfer line 19, and is thereby separated into an acrylic acid solution and a liquid byproduct. The separated acrylic acid solution is subjected to distillation and recrystallization, thus obtaining acrylic acid. The gas byproduct separated in the absorption tower is treated using the control unit 16 of the recycling transfer line 18, whereby the amounts of carbon dioxide and water vapor are adjusted so as to be adapted for mol % of the fresh feed, and thus the gas byproduct is partially split and is recycled.

In order to be adapted for the mol % of the fresh feed, propane and oxygen are added and combined with the gas byproduct, and the resulting stream is supplied into the partial oxidation reactor 11 via the transfer lines 18, 10. The recycling gas byproduct includes propylene, unreacted propane, carbon dioxide, and water vapor, and the total molar ratio of the recycling gas byproduct and the additionally supplied propane and oxygen may be adjusted so as to be uniform.

In a preferred embodiment of the present invention, the oxidation unit may be provided in the partial oxidation reactor, or may be disposed between the partial oxidation reactor and the absorption tower.

In order to increase contact efficiency of the acrylic acid-containing mixed gas and the absorption solvent, the absorption tower 14 may be provided in the form of a packed column with a filler such as a rashing ring, pall ring, saddle, gauze, or structured packing, or a typical multi-stage column.

Of the distillation tower 20, for example, a distillation tower 20a may be a low-boiling-point separation tower for separating aldehydes or alkenes, a distillation tower 20b may be used to separate acetic acid via the transfer line 22, and a distillation tower 20c may be a high-boiling-point separation tower for discharging crude acrylic acid via the top transfer line 21 and for discharging high-boiling-point material (waste oil) via the bottom transfer line 23.

For example, assuming that the use of 7% propane results in a conversion of 60%, a carbon monoxide (CO) selectivity of 10%, a carbon dioxide ($CO_2$) selectivity of 10% and an acrylic acid selectivity of 80%, the feed rate of the feed is shown at each position of the POA process in a steady state. In a start-up state, the flow rate of CO is zero, but the amount of produced CO is increased more than the amount of purged CO with the progression of the reaction, thus building up the concentration of carbon monoxide (CO). The composition of the feed in a start-up state is composed of 7% propane, 14% oxygen ($O_2$), 0% carbon monoxide (CO), 59% carbon dioxide ($CO_2$), and 20% water ($H_2O$), but in a steady state, the feed composition includes 7% propane, 14% $O_2$, 29.5% CO, 29.5% $CO_2$, and 20% $H_2O$. The concentration of CO is increased to 29.5%. Because CO is built up during the processing, the actual POA process preferably further includes removing CO through selective CO oxidation.

The actual POA process may be provided in the form of including selective CO oxidation as shown in FIG. 3.

The carbon monoxide (CO) oxidation unit may be disposed upstream of the POA reactor or downstream of the POA reactor. The selective CO removal unit may be disposed upstream of the POA reactor, and the CO removal performance ($CO + 1/2 O_2 \rightarrow CO_2$) may be calculated as follows. Assuming that the CO conversion is 87.7% and the use of 7% propane results in a conversion of 60%, a CO selectivity of 10%, a $CO_2$ selectivity of 10%, and an acrylic acid selectivity of 80%, the feed rate of the feed may be calculated at each position in the POA process including the CO removal in a steady state. The results are shown in Table 3 below. In the case where the selective CO removal unit is disposed downstream of the POA reactor, the feed rates may vary slightly.

MODE FOR INVENTION

A better understanding of the present invention may be obtained via the following examples, which are set forth to illustrate, but are not to be construed as limiting the scope of the present invention. The scope of the present invention is given by the claims, and also contains all modifications within the meaning and range equivalent to the claims. Unless otherwise mentioned, "%" and "part", indicating amounts in the following examples and comparative examples, are given on a weight basis.

PREPARATION EXAMPLE

Using the following hydrothermal synthesis process, a $MoV_aTe_bNb_cO_x$-based catalyst was prepared.

Solution A: 40.11 g of ammonium paramolybdate was dissolved in 400 ml of warm water and 7.97 g of ammonium vanadate was then dissolved. Telluric dihydride (12.0 g) was then dissolved. The resulting solution was cooled to 35° C.

Solution B: 110 ml of water was added with 20.62 g of oxalic dihydride and 4.65 g of niobic acid and heated for 1 hr, thus obtaining a uniform solution. This solution was cooled to 35° C.

Solution B was added to Solution A. The slurry was spray-dried using the inlet temperature of 200° C. and the outlet temperature of 110° C., thus obtaining a solid product.

The solid product was calcined at 200° C. for 2 hr in air and fired at 600° C. for 2 hr while the amount of oxygen in the nitrogen stream was maintained at 5 ppm or less. The solid was then ground, compressed, and sieved. The 60 to 80 mesh fractions were investigated, and a $Mo_{1.0}V_{0.3}Nb_{0.12}Te_{0.23}O_x$ catalyst therein was obtained. Here, x is the amount of oxygen bound to the other elements, and depends on their oxidation state.

EXAMPLE 1

Propane was charged in a stainless-steel reactor having an inner diameter of ¾ inches and containing 10 g of the catalyst prepared in the above Preparation Example and heated in a molten salt. Here, propane, oxygen, and water vapor in the amounts shown in Table 1 below were subjected to partial oxidation under conditions of a space velocity of 1400 hr$^{-1}$, 360° C. and 15 psi, thus producing an acrylic acid-containing gas. The acrylic acid-containing gas was passed through an absorption tower for spraying water from the top thereof, and was thereby separated into an acrylic acid-containing solution and a gas byproduct. Some of the gas byproduct separated in the absorption tower was split and removed in an amount corresponding to the amount of produced carbon dioxide. Also, propane and oxygen were further added in amounts corresponding to the decreased amounts through the reaction, compared to the molar ratio of the fresh feed, and thus combined with the gas byproduct, and the resulting stream was supplied into the fixed-bed reactor so as to reach a steady state. The acrylic acid-containing solution was separated into an acrylic acid solution and a liquid byproduct using a distillation tower via the transfer line. The separated liquid byproduct was analyzed through gas chromatography. The separated acrylic acid solution was subjected to distillation and recrystallization, thus yielding acrylic acid.

In a steady state after a reaction time of 2 hr, the recycling gas byproduct included propylene, unreacted propane, carbon monoxide, carbon dioxide and water vapor, and the feed rates of the recycling gas byproduct and the additionally supplied propane and oxygen are shown in Table 1 below.

TABLE 1

| Component | Feed rate at each position | | | |
|---|---|---|---|---|
| | Fresh feed | Line 10 | Line 13 | Line 18 |
| Propane | 4.49 | 7.00 | 2.8 | 2.51 |
| O$_2$ | 12.39 | 14.00 | 1.79 | 1.61 |
| N$_2$ | — | — | — | — |
| H$_2$O | — | 20.00 | 29.6 | 20.00 |
| AA | — | — | 3.36 | — |
| Propylene | — | 0.19 | 0.21 | 0.19 |
| Acetic acid (other oxygenated) | — | — | 0.084 | — |
| CO | — | 8.85 | 9.86 | 8.85 |
| CO$_2$ | — | 49.96 | 55.65 | 49.96 |

EXAMPLE 2

This Example was carried out through the process shown in FIG. 3.

Propane was charged in a stainless-steel reactor having an inner diameter of ¾ inches and containing 10 g of the catalyst prepared in the above Preparation Example and heated in a molten salt. Here, propane, oxygen, and water vapor in the amounts shown in Table 2 below were subjected to partial oxidation under conditions of a space velocity of 1400 hr$^{-1}$, 360° C. and 15 psi, thus producing an acrylic acid-containing gas. The acrylic acid-containing gas was passed through an oxidation unit 12 containing a Pt catalyst layer, whereby carbon monoxide was oxidized into carbon dioxide. Also, the acrylic acid-containing gas was passed through an absorption tower 14 for spraying water from the top thereof, and was thereby separated into an acrylic acid-containing solution and a gas byproduct.

Some of the gas byproduct separated in the absorption tower was split and removed in an amount corresponding to the amount of produced carbon dioxide. Also, propane and oxygen were additionally supplied so as to be suitable for the mol % of the fresh feed, and thus combined with the gas byproduct, and the resulting stream was supplied into the fixed-bed reactor so as to reach a steady state. The acrylic acid-containing solution was separated into an acrylic acid solution and a liquid byproduct using a distillation tower 20 via the transfer line 19. The separated liquid byproduct was analyzed through gas chromatography. The separated acrylic acid solution was subjected to distillation and recrystallization, thus yielding acrylic acid. In a steady state after a reaction time of 2 hr, the recycling gas byproduct included propylene, unreacted propane, carbon monoxide, carbon dioxide and water vapor, and the feed rates of the recycling gas byproduct and the additionally supplied propane and oxygen are shown in Table 2 below.

TABLE 2

| Component | Feed rate at each position | | | |
|---|---|---|---|---|
| | Fresh feed | Line 10 | Line 13 | Line 18 |
| Propane | 4.31 | 7.00 | 2.8 | 2.69 |
| O$_2$ | 10.66 | 14.00 | 3.47 | 3.34 |
| N$_2$ | — | — | — | — |
| H$_2$O | — | 20.00 | 29.8 | 20.80 |
| AA | — | — | 3.38 | — |
| Propylene | — | 0.55 | 0.55 | 0.57 |
| Acetic acid (other oxygenated) | — | — | 0.08 | — |

TABLE 2-continued

| | Feed rate at each position | | | |
|---|---|---|---|---|
| Component | Fresh feed | Line 10 | Line 13 | Line 18 |
| CO | — | 0.11 | 0.11 | 0.11 |
| $CO_2$ | — | 58.34 | 58.34 | 58.34 |

As is apparent from Table 2, the concentration of carbon monoxide (CO) supplied into the reactor in a steady state was maintained low, and thus CO concentration build-up problems like the case of example 1 did not occur. Hence, safe operation was possible.

COMPARATIVE EXAMPLE 1

Propane was charged in a stainless-steel reactor having an inner diameter of ¾ inches and containing 10 g of the catalyst prepared in the above Preparation Example and heated in a molten salt. Here, propane, oxygen, nitrogen, and water vapor in the amounts shown in Table 3 below were subjected to partial oxidation under conditions of a space velocity of 1400 $hr^{-1}$, 360° C. and 15 psi, thus producing an acrylic acid-containing gas. The acrylic acid-containing gas was passed through an absorption tower for spraying water from the top thereof, and was thereby separated into an acrylic acid-containing solution and a gas byproduct. The separated gas byproduct was incinerated in an incinerator, and the acrylic acid-containing solution was separated into an acrylic acid solution and a liquid byproduct via a distillation tower. The feed rates of individual components of the separated gas byproduct and liquid byproduct were calculated using gas chromatography. The results are given in Table 3 below. The total reaction time was 2 hr.

TABLE 3

| | Feed rate | |
|---|---|---|
| Component | Fresh feed | After Reaction |
| Propane | 7.00 | 2.90 |
| $O_2$ | 14.00 | 4.00 |
| $N_2$ | 59.00 | 59.00 |
| $H_2O$ | 20.00 | 29.10 |
| AA | | 3.20 |
| Propylene | | 0.02 |
| Acetic acid (other oxygenated) | | 0.08 |
| CO | | 1.00 |
| $CO_2$ | | 1.20 |

TEST EXAMPLE 1

The results of Examples 1 and 2 and Comparative Example 1 were calculated using the following equations. The results are shown in Table 4 below. The propane conversion and acrylic acid selectivity and yield are defined as follows:

Propane conversion (%)=(mol of reacted propane/mol of supplied propane)×100

Acrylic acid selectivity (%)=(mol of produced acrylic acid/mol of reacted propane)×100

Acrylic acid yield (%)=(mol of produced acrylic acid/mol of supplied propane)×100

TABLE 4

| Component | Example 1 | Example 2 | C. Example 1 |
|---|---|---|---|
| Conversion % | 93.5 | 97.4 | 58.6 |
| Selectivity % | 80.0 | 80.5 | 78.0 |
| Yield % | 74.8 | 78.4 | 45.7 |

TEST EXAMPLE 2

Example 2 and Comparative Example 1 were performed under the same conditions, and the reaction time was prolonged to 50 hr.

As results thereof, the acrylic acid conversion and selectivity were not changed under the conditions of Example 2. However, in Comparative Example 1, using nitrogen ($N_2$) as a carrier gas, the conversion was decreased from 35% to 23% due to the coke deposition on the catalyst. Also in Example 2, only oxygen and propane, which were deficient in the recycling gas byproduct, were additionally supplied, thus continuously preparing acrylic acid. In Comparative Example 1, however, not only the deficient oxygen and propane but also the nitrogen feed had to be continuously supplied. Furthermore, an additional step for separating carbon monoxide (CO) and carbon dioxide ($CO_2$) accumulated in the reactor was required. Hence, energy and cost were much lower in Example 2 than in Comparative Example 1.

Therefore, the method of continuously preparing acrylic acid according to the present invention can be concluded to be simplified and remarkably decreased in costs compared to the conventional method.

DESCRIPTION OF THE REFERENCE NUMERALS IN THE DRAWINGS

10: Feed transfer line, 18: Recycling transfer line
13, 15, 17, 19, 21, 22, 23: Transfer line
11: Partial oxidation reactor, 12: Oxidation unit, 14: Absorption tower, 16: Control unit, 20: Distillation tower

The invention claimed is:

1. A method of continuously preparing acrylic acid, comprising steps of:
    (1) subjecting a feed including propane, oxygen, water vapor and carbon dioxide to partial oxidation using a catalyst, thus obtaining an acrylic acid-containing mixed gas;
    (2) separating the acrylic acid-containing mixed gas into an acrylic acid-containing solution and a gas byproduct;
    (3) separating an acrylic acid solution from the separated acrylic acid-containing solution; and
    (4) recycling the separated gas byproduct into the feed, wherein an amount of the water vapor is 5 to 50 mol% based on a total mol% of the feed and an amount of the carbon dioxide is 40 to 80 mol% based on a total mol% of the feed, and
    wherein nitrogen is not included in the feed.

2. The method of claim 1, wherein the gas byproduct includes at least one selected from the group consisting of propane, propylene, oxygen, carbon monoxide, carbon dioxide, and water vapor.

3. The method of claim 1, wherein the separated gas byproduct of the step (4) is recycled so as to be suitable for a composition molar ratio of the feed in the step (1).

4. The method of claim 1, further comprising oxidizing carbon monoxide into carbon dioxide using a catalyst including at least one selected from the group consisting of rhodium (Rh), iridium (Ir), palladium (Pd), and platinum (Pt), between the steps (1) and (2).

5. The method of claim 1, further comprising oxidizing carbon monoxide into carbon dioxide using a catalyst including at least one selected from the group consisting of rhodium (Rh), iridium (Ir), palladium (Pd), and platinum (Pt), during recycling from the step (4) to the step (1).

6. The method of claim 1, wherein a molar ratio of the propane to the oxygen is 1:0.5 to 3.

7. The method of claim 1, wherein the catalyst is represented by Chemical Formula 1 below:

$$MoV_aTe_bNb_cO_x \qquad \text{[Chemical Formula 1]}$$

in Chemical Formula 1,
a is a number from 0.006 to 1,
b is a number from 0.006 to 1,
c is a number from 0.006 to 1, and
x is an amount of oxygen bound to other elements and depends on their oxidation state.

8. The method of claim 1, wherein the partial oxidation is carried out at 200 to 500° C.

9. The method of claim 1, wherein the step (b) is performed using an absorption solvent, and the absorption solvent is water.

10. An apparatus for continuously preparing acrylic acid according to the method of claim 1, comprising:
(1) a partial oxidation reactor configured to prepare an acrylic acid-containing mixed gas by subjecting a feed including propane, oxygen, water vapor and carbon dioxide, transferred via a feed transfer line, to partial oxidation using a catalyst;
(2) an absorption tower configured to separate the acrylic acid-containing mixed gas into an acrylic acid-containing solution and a gas byproduct and to absorb the acrylic acid-containing solution;
(3) a distillation tower configured to separate the acrylic acid-containing solution into an acrylic acid solution; and
(4) a recycling transfer line configured to recycle the separated gas byproduct.

11. The apparatus of claim 10, wherein the recycling transfer line is connected to the feed transfer line or the partial oxidation reactor.

12. The apparatus of claim 10, further comprising an oxidation unit containing a catalyst including at least one selected from the group consisting of rhodium (Rh), iridium (Ir), palladium (Pd), and platinum (Pt).

13. The apparatus of claim 10, wherein the gas byproduct includes at least one selected from the group consisting of propane, propylene, oxygen, carbon monoxide, carbon dioxide, and water vapor.

14. The apparatus of claim 10, further comprising a control unit configured to control the recycling gas byproduct so as to be suitable for a composition molar ratio of the feed, wherein the control unit is provided to the recycling transfer line.

15. The apparatus of claim 10, wherein a molar ratio of the propane to the oxygen is 1:0.5 to 3.

16. The apparatus of claim 10, wherein the catalyst is represented by Chemical Formula 1 below:

$$MoV_aTe_bNb_cO_x \qquad \text{[Chemical Formula 1]}$$

in Chemical Formula 1,
a is a number from 0.006 to 1,
b is a number from 0.006 to 1,
c is a number from 0.006 to 1, and
x is an amount of oxygen bound to other elements and depends on their oxidation state.

17. The apparatus of claim 10, wherein the partial oxidation is carried out at 200 to 500° C.

18. The apparatus of claim 10, wherein separation in the absorption tower is performed using an absorption solvent, and the absorption solvent is water.

* * * * *